(12) United States Patent
Khulusi

(10) Patent No.: US 7,062,797 B2
(45) Date of Patent: Jun. 20, 2006

(54) MULTI-PURPOSE GOGGLE

(76) Inventor: Basimah Khulusi, 930 Broadway, Suite 401, Kansas City, MO (US) 64105

( * ) Notice: Subject to any disclaimer, the term of this patent is extended or adjusted under 35 U.S.C. 154(b) by 0 days.

(21) Appl. No.: 11/123,547

(22) Filed: May 5, 2005

(65) Prior Publication Data

US 2005/0229294 A1    Oct. 20, 2005

Related U.S. Application Data

(63) Continuation-in-part of application No. 10/691,189, filed on Oct. 22, 2003.

(60) Provisional application No. 60/420,822, filed on Oct. 24, 2002.

(51) Int. Cl.
*A61F 9/02* (2006.01)

(52) U.S. Cl. ............................................. 2/431; 2/435

(58) Field of Classification Search .................. 2/9, 2/12, 15, 436, 427, 441, 439, 444, 447, 449; 351/43, 41, 44, 62, 159
See application file for complete search history.

(56) References Cited

U.S. PATENT DOCUMENTS

| 2,422,534 A | * | 6/1947 | Du Bois | 2/441 |
| 3,031,674 A | * | 5/1962 | Ring | 2/441 |
| 4,850,058 A | * | 7/1989 | Cheng | 2/439 |
| 5,138,723 A | * | 8/1992 | Bolle | 2/430 |

* cited by examiner

*Primary Examiner*—Katherine M. Moran
(74) *Attorney, Agent, or Firm*—Lathrop & Gage LC

(57) ABSTRACT

A multi-purpose goggle for protecting the eyes of the wearer in industrial and sporting environments and against glare when the wearer is viewing a computer screen for extended periods of time, for housing a virtual reality display and for use by pilots engaged in training for their instrument flight rating. The goggle housing is comprised of a downwardly extending upper surface with a first end and a second end, a viewing area operatively configured in some embodiments for receiving an insert, a centrally disposed nose bridge and a first and second lower panel disposed opposite the nose bridge and a securing means comprised of rearward extensions of the upper surface and lower panels.

41 Claims, 10 Drawing Sheets

MULTI-PURPOSE GOGGLE

RELATED APPLICATION

This continuation-in-part application of U.S. patent application Ser. No. 10/691,189, filed Oct. 22, 2003, which claims benefit of U.S. patent application Ser. No. 60/420,822, filed Oct. 24, 2002, both of which are incorporated herein by reference.

FIELD OF THE INVENTION

This invention relates generally to a multi-purpose goggle that can be utilized as a safety goggle suitable for a wide range of activities including: industrial and sporting use as well as a goggle to minimize or eliminate computer vision syndrome resulting from the prolonged use of a computer display terminal, as a platform for a virtual reality visor and for a limited viewing goggle for pilots undergoing instrument flight rating ("IFR") qualifications. The goggles are configured such that they can be easily manufactured and utilized.

DESCRIPTION OF THE RELATED ART

Virtually all industrial and sports injuries to the eye are avoidable if suitable eye protection such as goggles are provided. Eye trauma is the leading cause of blindness worldwide. It is estimated that each day two thousand individuals in the United States suffer eye injuries on the job or while playing sports. These injuries incur more than $924 million annually in worker's compensation, and nearly $4 billion in wage and productivity losses according to the U.S. Bureau of Labor Statistics. Nearly 90 percent of all workplace and sports related injuries are preventable with the proper eyewear and safety measures according to statistics from the organization Prevent Blindness America.

It is evident from the eye injury statistics that large numbers of individuals are not wearing eye protection while in the vicinity of activities that present dangers to the eye. Also, injuries are still occurring despite the use of protective eyewear. Those individuals being injured often wear inappropriate or ill-fitting eyewear for the task being undertaken or do not wear protective eyewear at all times while undertaking the task. The literature suggests that the main reasons individuals do not wear protective eyewear relate to issues of comfort, style, restricted vision, and safety equipment not provided by employers.

OSHA standards require that employers provide, and workers wear, suitable eye protection. To be effective, the eyewear must be the appropriate type and properly fitted. For example, the Bureau of Labor Statistics survey revealed that 94 percent of injuries to workers wearing eye protection resulted from objects or caustics going around or under the protector. But less than six percent of the injuries happened to workers wearing goggles, which generally offer a tighter fit around the eyes.

Wearing protective eyewear can prevent 90% of sports-related injuries. Eyeglasses and contact lenses do not provide protection and can even place an athlete at an increased risk for such injuries. The American Academy of Ophthalmology has instituted a campaign for mandatory eyewear for children participating in school-related or community-sponsored athletic events. The Academy recommends that young athletes wear shatterproof goggles, constructed of 3 mm polycarbonate, that are fitted by an eye care professional.

In general, those individuals that are injured often wear inappropriate safety or ill-fitting eyewear for the task being undertaken, or do not wear protective eyewear at all times while undertaking the task. The finding that safety glasses may not provide adequate protection against small, off-center particles needs to be addressed, and the use of goggles promoted. According to OSHA, eye protection must, protect against the specific hazard(s) encountered in the workplace, be reasonably comfortable to wear, not restrict vision or movement, be durable and easy to clean and disinfect and not interfere with the function of other required personal protection equipment.

The reasons people give for not wearing safety goggles include, the safety goggles cause headaches, the eye protection is too hot to wear, the goggles are constantly dirty, the eye protection fogs over, the safety glasses never fit correctly, the goggles do not fit over prescription eyeglasses, the goggles lack style or comfort, and cause distortion and limit the field of vision.

Information relevant to attempts to address these problems can be found in U.S. Pat. Nos. 5,966,746, 5,519,896, 6,357,053, 5,771,499 and 6,178,561. However, each of these references suffers from one or more of the following disadvantages: inability to use existing prescription glasses while wearing the goggles, excessive goggle weight, limitations on range of vision such as obstruction of peripheral vision, uncomfortable to wear because of pressure applied to the head by bands and straps and internal fogging of the lenses brought about by perspiration, and at times respiration, of the wearer.

In addition to the ability of the multi-purpose goggles to protect against injury to the eye in sporting as well as industrial settings, the present invention is also well adapted to protect the eyes against computer vision syndrome. This condition most commonly occurs when the viewing demand of the task exceeds the visual abilities of the display terminal user. The symptoms of computer vision syndrome can be diminished, or eliminated, if proper equipment is employed. The American Optometric Association defines computer vision syndrome as that complex of eye and vision problems related to near work which are experienced during or related to computer use. The symptoms can vary, but they include eyestrain, headaches, blurred vision (distance, near, or both), dry and irritated eyes, slowed refocusing, neck ache, backache, sensitivity to light, and double vision.

Discomfort from glare is caused primarily by great disparities in brightness in the field of view. It is much more desirable to eliminate bright sources of light from the field of view and to strive to obtain a relatively even distribution of luminaries. A person is at great risk of experiencing discomfort from glare when the source of light is brighter and closer to the point of attention. For example, seventy five percent of the people who suffer from computer vision syndrome are those who wear eyeglasses. One of the primary reasons that discomfort glare is a problem for computer users is that light often leaves the overhead fluorescent fixture in a wide angle, resulting in light directly entering the worker's eyes. This is particularly a problem for computer workers because they are generally looking horizontally into the screen. A secondary cause of discomfort glare is the reflection of light by the lenses of the eyeglasses in proximity to the eye of the wearer.

The opaque embodiment of the present invention attempts to utilize the compact geometry of the goggle and its various surfaces such as the upper surface and the lower panels to protect the eyes of the wearer and to minimize the transmission of light rays that ultimately reach the eyes other then through the centrally disposed viewing area.

In addition to the above objectives, the multi-purpose goggle is well suited for use as a virtual reality visor. A virtual reality system generally comprises a display/sensor apparatus that is worn by a viewer and connected to a computer system capable of manipulating the position and perspective of the image viewed in the display to correspond with the position from which it is being viewed. The present invention will eliminate glare from around the screen of the virtual reality visor while providing the wearer with a comfortable goggle.

It is a problem in complex computer controlled systems that deal with real world phenomena to present a representation of the phenomena in a manner that is both informative to the user and in a simple presentation format. Computer generated graphics are ubiquitous and are typically used to present an accurate representation of an object in a multi-dimensional space and the interactions therebetween. Computer generated graphics are also used extensively in simulation systems to present an image of a real world situation or a hypothetical situation to a user for training, analysis or other purposes. Computer generated graphics have become extremely sophisticated and can represent extremely complex and fanciful situations in a manner that is virtually lifelike.

One area in which computer graphics is making a significant impact is the area of real time display of complex real world phenomena. Goggle mounted display devices (GMD's) are increasingly being utilized for virtual reality and "Telepresence" applications. Such devices generally consist of one or more compact image displaying devices mounted on a goggle type frame that the viewer wears on their head. The said image displaying devices project images into the viewer's eyes via a series of lenses or mirrors so that the viewer perceives the image or images to originate from a source outside of the goggle. In the case of stereoscopic GMD's a separate image is presented to each of the viewer's eyes so that a three dimensional (3D) image can be formed. This 3D image has the additional reality of 3D depth cues such as stereo parallax (the differential shifting of objects within the image due to varying distance from the camera or other imaging source).

Lastly, the multi-purpose goggle can be used in training by instructors to teach student and experienced pilots to recover from unusual situations. The goggles mimic instrument conditions—generally those in which visibility is less than three miles—by placing over the student's head a goggle that acts like a blinder, allowing for a view of the cockpit instruments but not of the scene that fills the window.

Therefore, it is an object of the present invention to provide an improvement in the structure of multi-purpose goggles which can obviate or substantially lessen the potential for physical objects impacting the eyes, protecting the eyes from glare that can induce computer vision syndrome, serving as a virtual reality goggle or a partial blinder in a training session for a pilot pursuing her instrument flight rating qualifications or seeking to refresh them.

SUMMARY OF THE INVENTION

The present invention is directed to multi-purpose goggles that satisfy the demand for maximizing wearing comfort through ergonomic construction, maximizing field of view, minimizing distortion, minimizing fogging, reduces or eliminates computer vision syndrome, provides an ideal platform for a virtual reality display system and functions superbly in the training of pilots seeking their instrument flight rating wherein it can serve to allow viewing of the cockpit instruments but not of the scene that fills the window.

A goggle having features of the present invention comprises a downwardly extending upper surface with a first end and a second end, a centrally disposed viewing area, a centrally disposed nose bridge and a first and second lower panel disposed opposite one another from the nose bridge. The first and second lower panel join the upper surface proximate the upper surface first end and second ends while the posterior edge of the upper surface is contoured to conform to the topography of the wearer's face.

Vents are optionally disposed in the goggle and means for supporting the goggle on the head of the wearer are also incorporated. When needed for eye protection in industrial and sporting situations the centrally disposed viewing area is operatively configured for receiving a translucent insert that protects against objects impacting the eyes of a wearer. The translucent insert is preferably constructed of a shatterproof polycarbonate; however, other materials possessing similar characteristics may also be utilized.

The goggle is preferably constructed in one of several embodiments of either a translucent material or an opaque material. Specifically, with an opaque goggle, the centrally disposed viewing area can be configured to remain open as in the case of a goggle to protect against computer vision syndrome. Another embodiment would utilize a translucent goggle and receive a translucent shatter resistant insert that fills the entire open frontal area as in the case of a goggle that is used in an industrial or sports setting. Another embodiment would utilize an opaque goggle and an opaque insert that partially fills the centrally disposed viewing area and can be utilized, for example, for protecting against the onset of computer vision syndrome or in the training of pilots seeking instrument flight rating qualifications. The opaque insert would fill only a portion of the centrally disposed viewing area allowing the pilot-in-training a view of the cockpit instruments but not of the scene that fills the window of the airplane.

Another embodiment of the present invention would utilize a virtual reality viewing system to be received into the centrally disposed viewing area of an opaque goggle thereby allowing the eyes of the wearer to be positioned in close proximity to the display system. The lightweight ergonomic goggle coupled with a compact virtual reality viewing system would create an ideal combination that minimizes wearer fatigue and maximizes viewing comfort. Moreover, the goggle eliminates glare from around the screen area. Also, the rearward extension of the upper surface and lower panels will conceal the wires leading to the virtual reality display device from the central processing unit and can provide space for additional componentry as required.

As mentioned above, translucent goggles are utilized in industrial and sports related settings where maximum observability in all directions is critical to the wearer. The ability to view objects overhead, peripherally and beneath the wearer are critical in certain settings and vision cannot be obstructed without threatening the safety of the wearer.

The present invention is preferably constructed with the centrally disposed viewing area substantially open; however, an alternative embodiment would have the centrally disposed viewing area of the translucent goggle filled with the same translucent material as the remainder of the goggle.

This embodiment would negate the need for an insert as the shielding effect of the closed frontal area would thereby be accomplished.

The upper surface conforms to the head of the wearer and is configured to accommodate the glasses of a wearer and also preserve the ability of the wearer to see superiorly, laterally and inferiorly to increase the field of vision or view when translucent materials are utilized.

Because of the ergonomic design, the goggle is capable of accommodating a large range of facial topographies and can also accommodate a substantial variety of glasses without the goggle being excessively heavy or producing the sensation that the goggle is attempting to fall from the face of the wearer. The goggle of the present invention is scalable and can be produced in a variety of sizes. The radius of the upper surface can be adjusted during the manufacturing process to produce goggles for children and adults alike by varying the radius dimension associated with the upper surface and other critical dimensions.

The preferred embodiment has an upper surface, a centrally disposed viewing area through which the wearer is able to see through or into which can be placed a virtual reality viewing display device, a centrally disposed nose bridge and two lower panels disposed opposite the nose bridge from each other and joining the upper surface at the opposite ends of the upper surface. The posterior edges of the upper surface and lower panels are contoured to conform to the topography of the individual's face and can utilize vents that are optimally located to facilitate movement of air that prevents fogging of the interior surfaces particularly of the inserts that may be received within the viewing area to protect the eyes of the wearer. The goggle upper surface and lower panels extend rearwardly from the face of and toward the ears of the wearer. The goggle preferably employs a head band apparatus that encircles the head of the wearer and supports the goggle on the head of the wearer.

This multi-purpose goggle has a unique ergonomic design, fashionable, sleek and futuristic looking and is contoured to conform to the topography of the individual's face therefore requiring a minimum amount of tension with a head band to hold it in position on the head of the wearer. The sleek ergonomic design is light in weight and evenly distributes a force across the posterior edges of the upper surface and lower panels thereby maximizing user comfort.

Usually, goggles pinch the eyeglasses at the nose bridge area or at the temple arms. Goggles are typically made to accommodate eyeglasses by making them oversized. Over sizing adds to the weight and interferes with their cosmetic appearance and comfort, thus resulting in non-use and subsequent eye injuries. The multi-purpose goggle of the present invention is uniquely designed to accommodate eyeglass frames and temple arms. The goggle's design provides a large open frontal area that facilitates viewing. Also, the securing apparatus exhibits a wedge shaped space to accommodate the temple arms of the eyeglasses and the goggle design accommodates a wide range of eyeglass frames.

Because this goggle conforms to the face of the wearer and has support means that consist of rearward extension of the upper surface and the lower panels, the head-encompassing member maintains the position of the goggle against the face of the wearer with the least amount of pressure. The head-encompassing member and the padding facilitate the formation of a seal between the posterior edges of the upper surface and lower panels and the face of the user that limits the entry of debris, chemicals or light to the eye.

These and other features, aspects, and advantages of the present invention will become better understood with reference to the following description, appended claims and accompanying drawings.

DETAILED DESCRIPTION OF THE INVENTION

Figure 1:
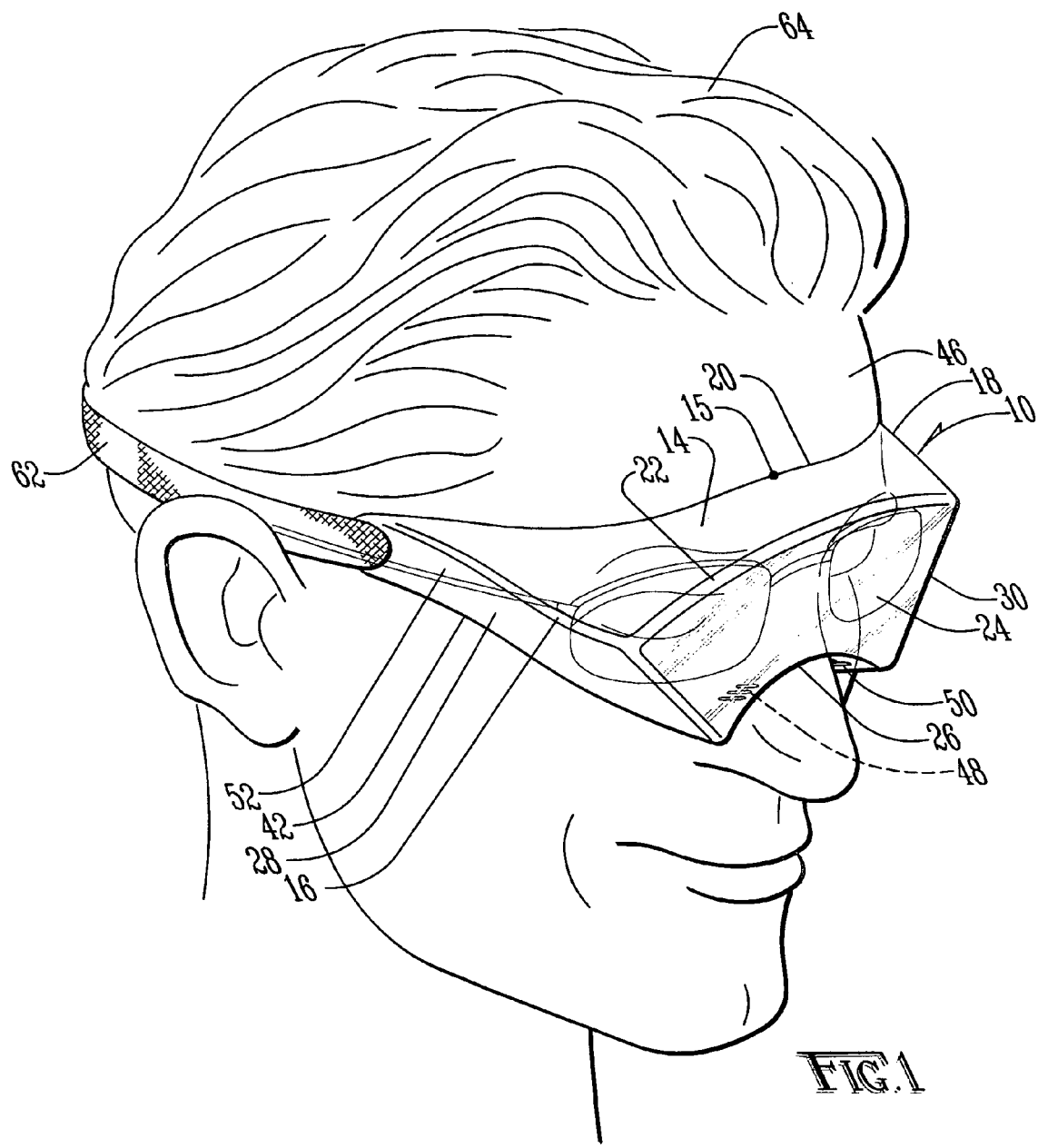
FIG. 1 is a perspective view of a multi-purpose goggle constructed of translucent material in accordance with a first embodiment of the present invention and positioned on the face of a wearer.

The preferred embodiment and best mode of the present invention is shown in FIG. 1. At FIG. 1, a multi-purpose goggle 10 constructed in accordance with the teachings of the present invention is shown generally at 10. A first translucent embodiment of the present invention is principally directed to use by individuals engaged in sporting events or at industrial work settings that may potentially be harmful to the eyes if the wearer lacks protection. Examples of sporting events for which these goggles would be appropriate are racquetball, skiing, basketball and baseball among many others activities. All of which incorporate a ball moving at a high rate of speed or the potential for eye injury through impact with other individuals or inanimate objects.

In industrial settings, for example, flying debris or splashing chemicals present a persistent threat to the safety of the eye and must be guarded against. In these settings a goggle of translucent material such as clear polycarbonate is required to enable the wearer to clearly and fully observe her surroundings.

Figure 2:
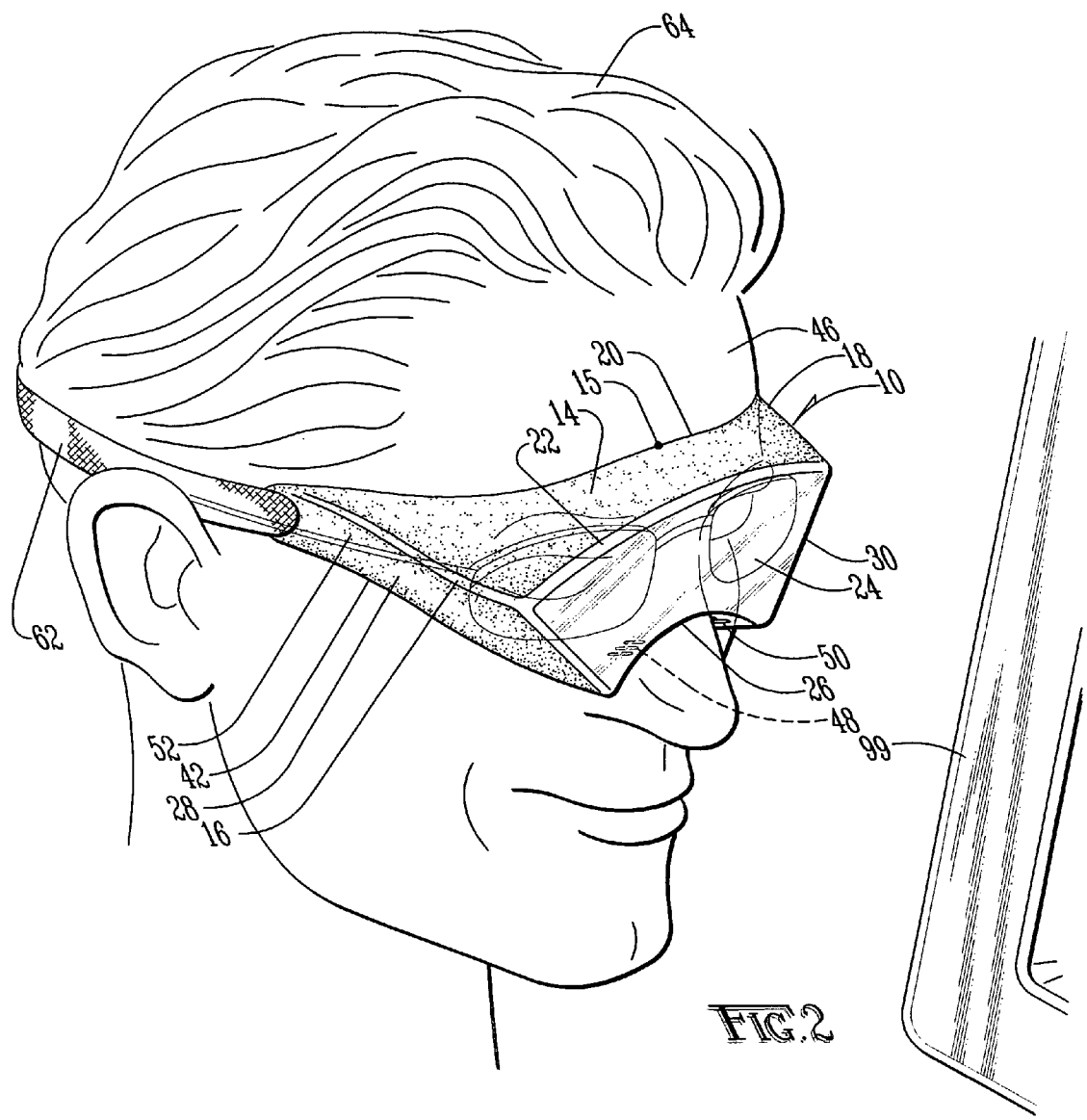
FIG. 2 is a perspective view of a multi-purpose goggle constructed of opaque material in accordance with a second embodiment of the present invention and positioned on the face of a wearer.

In situations where the wearer is engaged in viewing a computer monitor, a second embodiment of the present invention comprises an opaque goggle. FIG. 2 reveals a goggle embodiment similar to that in FIG. 1 except utilizing an opaque upper surface 14 and lower panels 28, 30 that prevent the transmission of undesirable light to the eyes of the wearer from sources other than the computer monitor 99 through the centrally disposed viewing area 24 thereby reducing or even potentially eliminating computer vision syndrome in some users.

Figure 3:
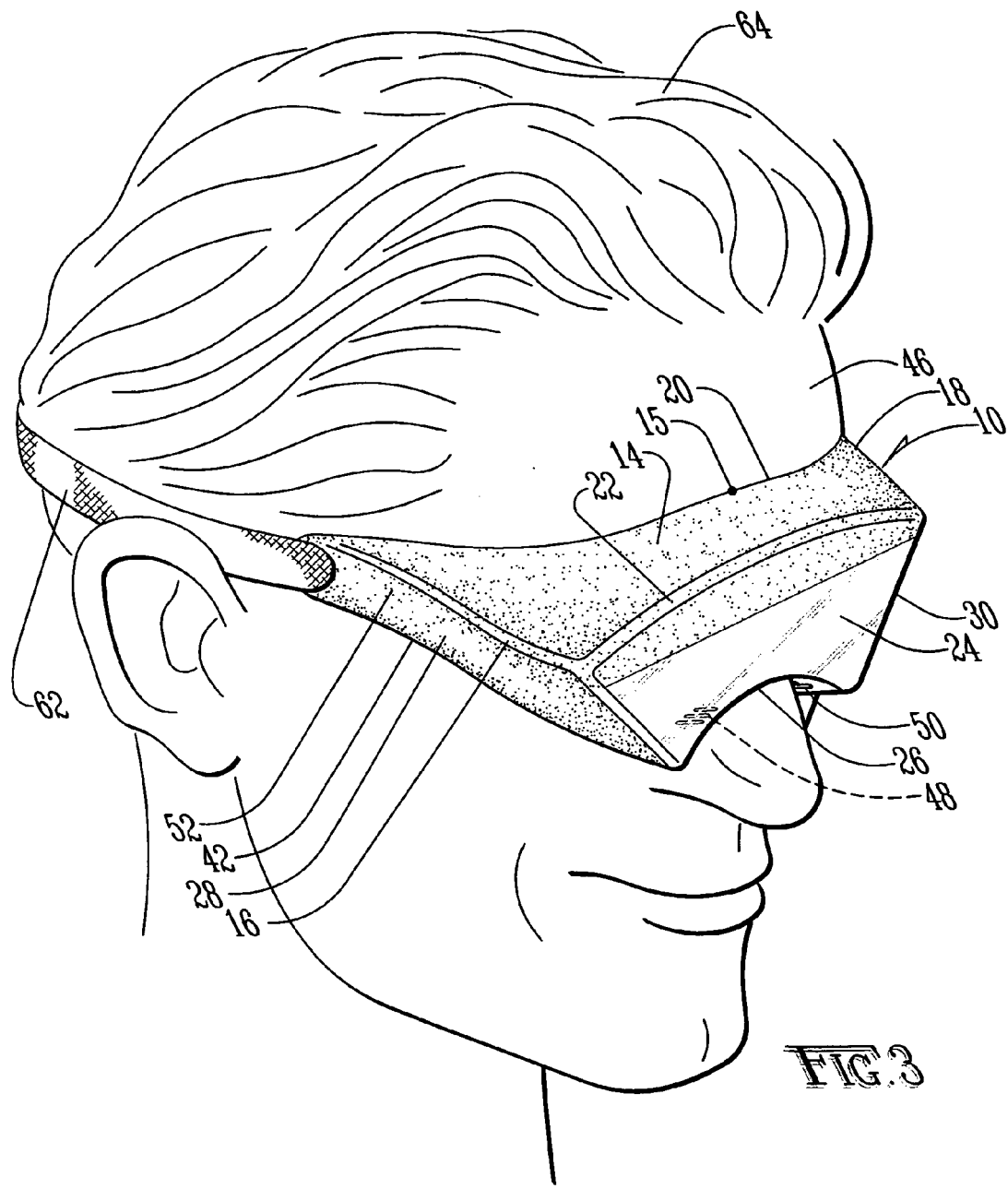
FIG. 3 is a perspective view of a multi-purpose goggle constructed in accordance with a third embodiment of the present invention, positioned on the face of a wearer and configured for pilot instrument flight rating training or for use in preventing or minimizing computer vision syndrome.

As seen in FIG. 3 a third embodiment with an opaque upper surface 14 and lower panels 28, 30 can also be utilized in settings where a student pilot or an experienced pilot undergoing a refresher course of instrument flight rating training has their field of vision restricted to just the cockpit instruments. The use of a detachable insert 110 or a goggle embodiment containing a centrally disposed viewing area 24 that has been reduced in size to facilitate this type of training will be discussed more fully below.

Figure 4:
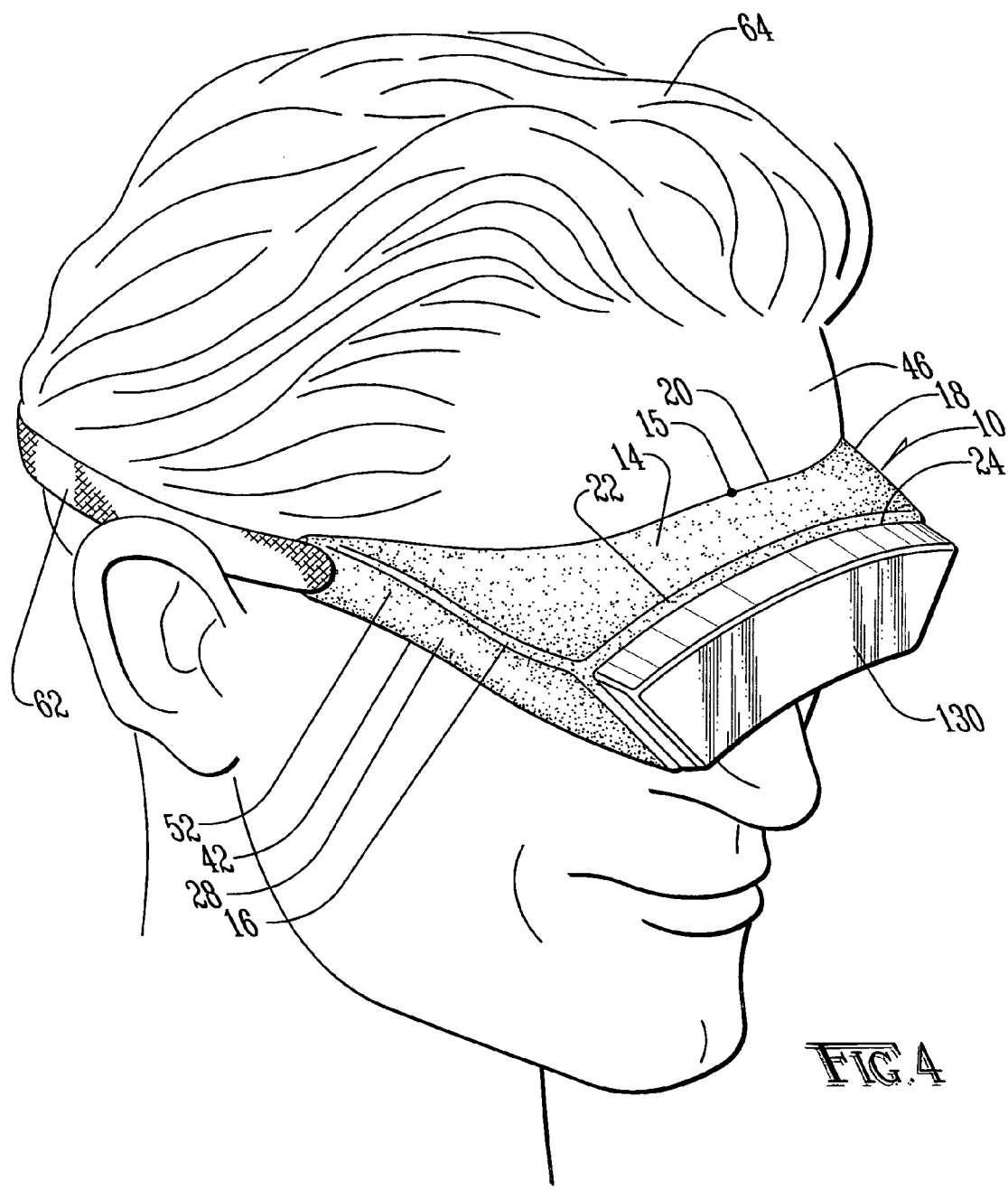
FIG. 4 is a perspective view of a multi-purpose goggle constructed in accordance with a fourth embodiment of the present invention, positioned on the face of a wearer and configured for receiving a virtual reality display.

FIG. 4 depicts a fourth embodiment of the multi-purpose goggle 10 that serves as a platform for a virtual reality display. The virtual reality display device 130 is preferably detachably secured to the goggle. The lightweight, ergonomic design and construction of the multi-purpose goggle 10 creates a superb platform for mounting of the virtual reality display device 130 in the centrally disposed viewing area 24.

Figure 5:
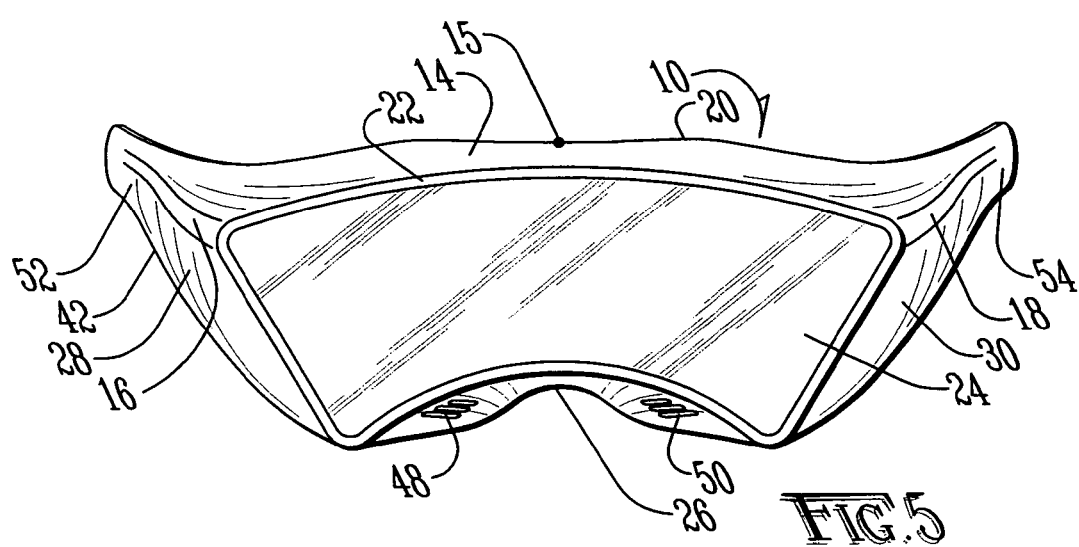
FIG. 5 is an elevation view of the front of a multi-purpose goggle of the present invention.

When viewed from the front of the goggle 10, as seen in FIG. 5, the upper surface 14 can be clearly seen merging with the first and second lower panels 28, 30. The viewing area 24 is preferably centrally disposed and comprised of a single viewing area; however, alternative embodiments may employ more than one viewing area 24 that is divided, for example, equally in half at the center of the nose bridge 26.

As shown in FIGS. 1 through 4, the protective goggle 10 includes an upper surface 14 that extends downwardly from the face 46 of the wearer. The upper surface 14, as measured from the center point 15 of the upper surface adjacent the posterior edge 20, extends downwardly from the face 46 of the wearer in the range of 10 to 40 degrees, and preferably between 20 and 30 degrees, from the horizontal. Additionally, as seen in FIGS. 1 and 5 the upper surface 14 traverses from one side of the face 46 of the wearer to the other side commencing in a first end 16 and terminating at a second end 18. The upper surface 14 further comprises a posterior edge 20 and an anterior edge 22.

Figure 6:
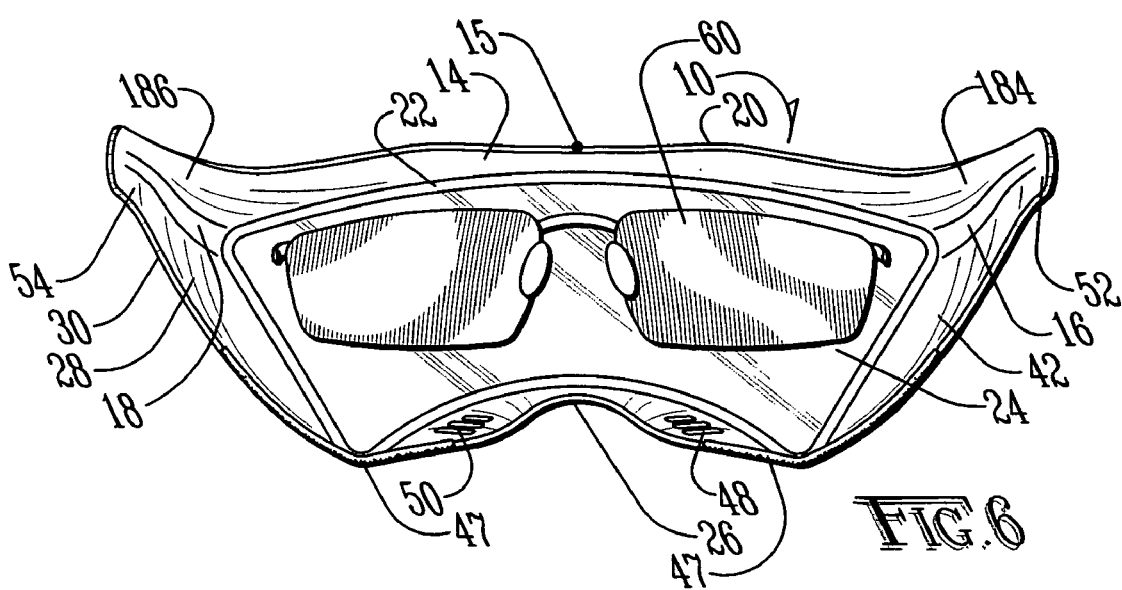
FIG. 6 is an elevation view of the interior of a multi-purpose goggle of the present invention with eye glasses disposed therein.

The goggle 10 further includes a centrally disposed viewing area 24, a centrally disposed nose bridge 26 and a first and second lower panel 28, 30 disposed opposite one another from the nose bridge 26. The upper edges 184, 186 of the first and second lower panels 28, 30 join the upper surface 14 at the first end 16 and second end 18. The upper edges 184, 186 are not constrained to be linear but may be curvilinear in configuration. As seen in FIG. 6, the lower panels 28, 30 also include edges 42, 44 contoured to conform to the topography of the face 46 of the wearer. The upper surface 14 is contoured to conform to the topography of the wearer's face 46 along a posterior edge 20 and preferably incorporates foam padding 47 to improve wearing comfort.

Figure 9:
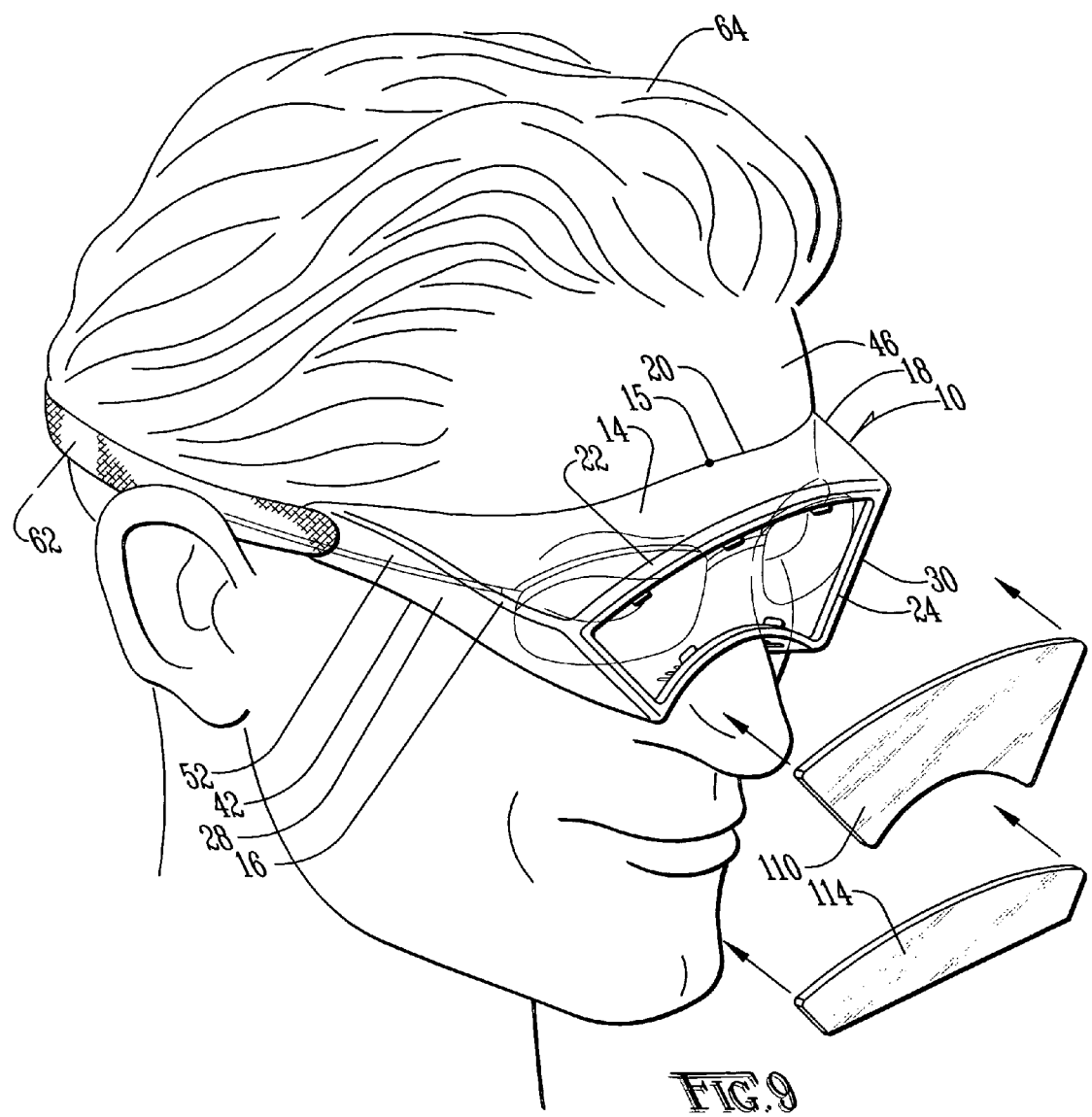
FIG. 9 is a perspective view of the open frontal area of a multi-purpose goggle of the present invention showing a translucent insert being received into the centrally disposed viewing area.

A preferred embodiment incorporates the placement of vents 48, 50 adjacent the nose bridge 26 to allow the discharge of moisture laden air out of the goggle minimizing fogging when an insert 110, as seen in FIG. 9, is positioned within the centrally disposed viewing area 24. If a full insert 110 were received into the viewing area 24 and vents 48, 50 were not utilized, perspiration from the face of the wearer 46 could potentially cause fogging of the insert 110 and obstruct the vision of the wearer.

Embodiments one through four can incorporate a translucent full insert 110 that is configured for insertion into and removal from the centrally disposed viewing area 24 depending upon the needs of the user. The full insert 110 can be placed into the centrally disposed viewing area 24 and held in position by a series of clips 32 attached to the upper surface 14 and the lower panels 28, 30. It will be appreciated by those skilled in the art that there are a variety of means for attachment of the clips 32. It will also be appreciated by those skilled in the art that the clips 32 must be appropriately positioned on the goggle 10 to securely maintain the full insert 110 in position. The full insert 110 is preferably comprised of a translucent shatterproof polycarbonate; however, other materials with similar translucent and shatterproof characteristics may be substituted for polycarbonate.

As seen in FIG. 9, the goggle 10 is capable of receiving inserts of varying sizes depending upon the particular needs of the goggle wearer. For example, a full transparent insert 110 is used principally in industrial and sports settings to protect the eyes of the wearer from contact with high speed objects, high temperature materials or caustic chemicals. In another situation, an opaque partial insert 114 is typically utilized with an opaque goggle 10 when a student is training for their instrument flight rating qualification and must have their field of vision limited to the controls within the cockpit. Alternatively, as seen in FIG. 4, a virtual reality display device 130 can be received into the centrally disposed viewing area 24 of an opaque goggle 10.

Figure 10:
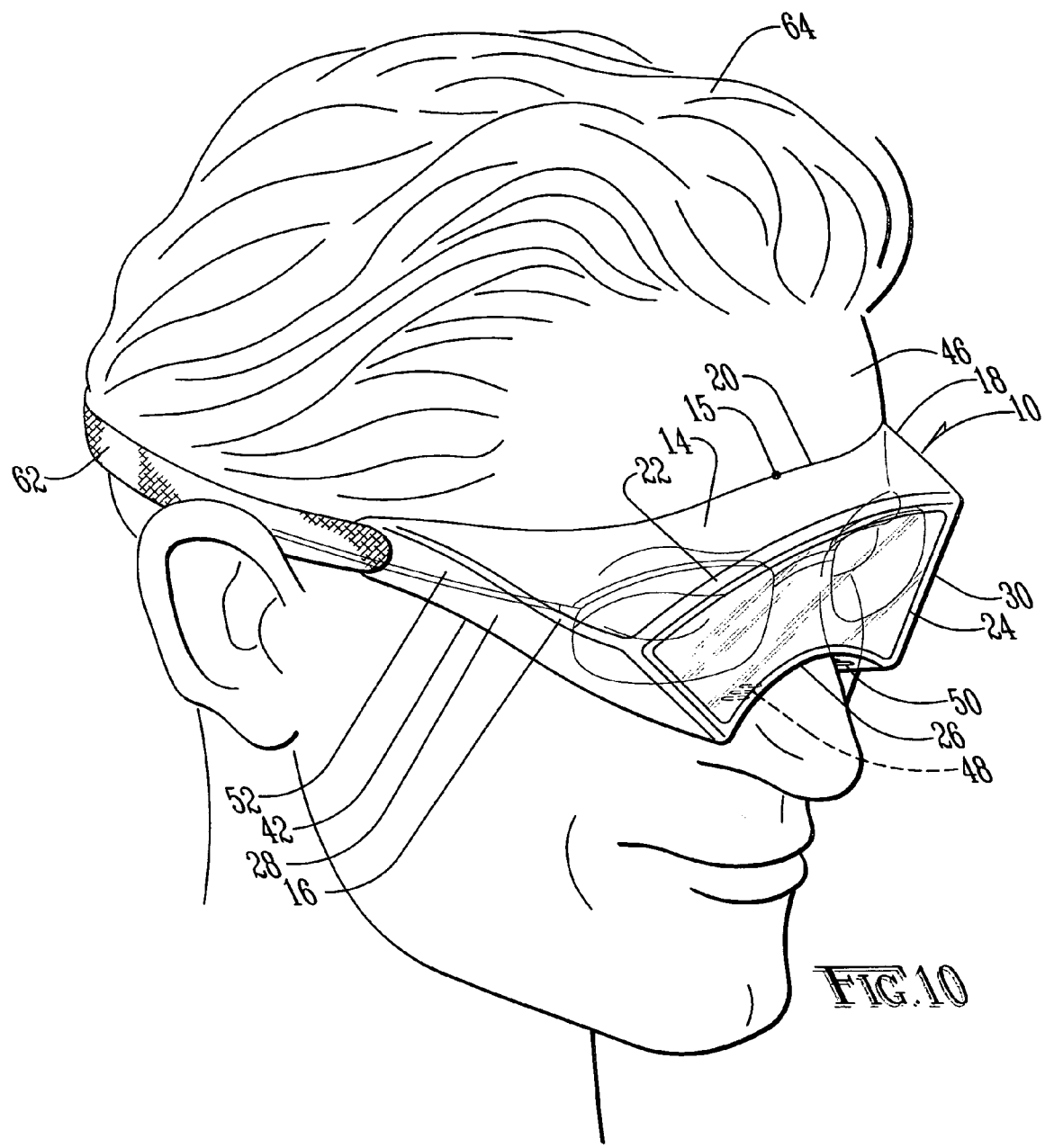
FIG. 10 is a perspective view of a multi-purpose goggle of the present invention with the centrally disposed viewing area enclosed.

As seen in FIG. 10, a fifth embodiment of the goggle 10 can be injection molded with the viewing area 24 enclosed by translucent material to provide maximum protection to the eyes of the wearer against, for example, intrusion by foreign objects or caustic chemicals. In this fifth embodiment, the first and second lower panels 28, 30 would, in effect, extend across the centrally disposed viewing area 24 thereby negating the need for an insert to protect the wearer against eye injury.

Figure 7:
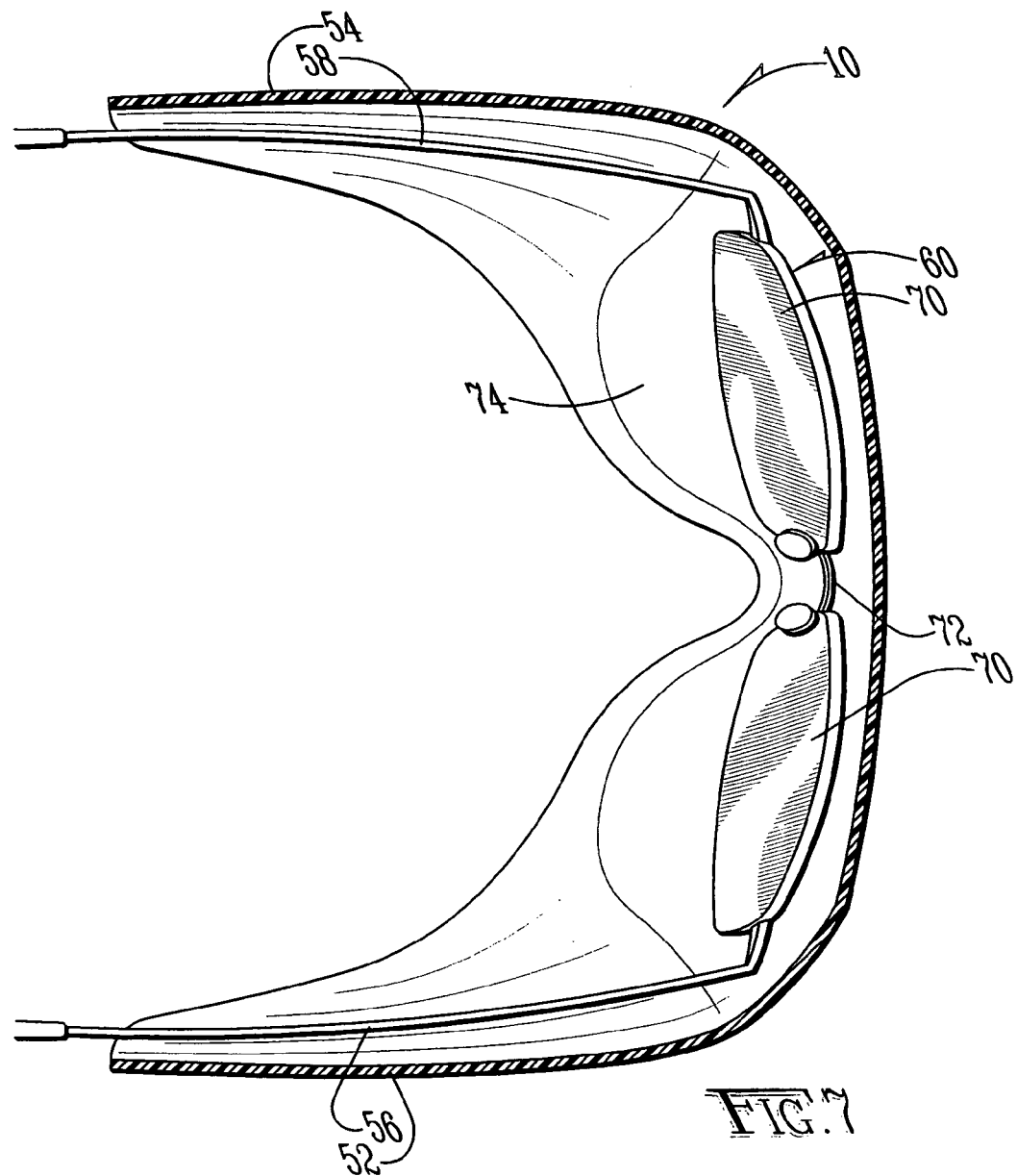
FIG. 7 is a top plan view of a multi-purpose goggle of the present invention with an eyeglasses frame and lenses disposed therein.

The upper surface 14 extends into support arms 52, 54 that traverse rearwardly towards the user's ears approximately 3 to 5 inches from the centrally disposed viewing area 24. As seen in FIG. 7, the support arms 52, 54 are sufficiently robust in their wedge shaped dimensions in order to accommodate the passage of the arms 56, 58 of a pair of glasses 60 back to the ears of the wearer. At the same time, the support arm 52, 54 dimensions are preferably minimized to reduce weight and to increase wearing comfort. The goggles 10, as best seen in FIGS. 1, 8 and 9 also utilize a strap 62 or other appropriate securing device to support the goggle 10 on the head 64 of the wearer.

Figure 8:
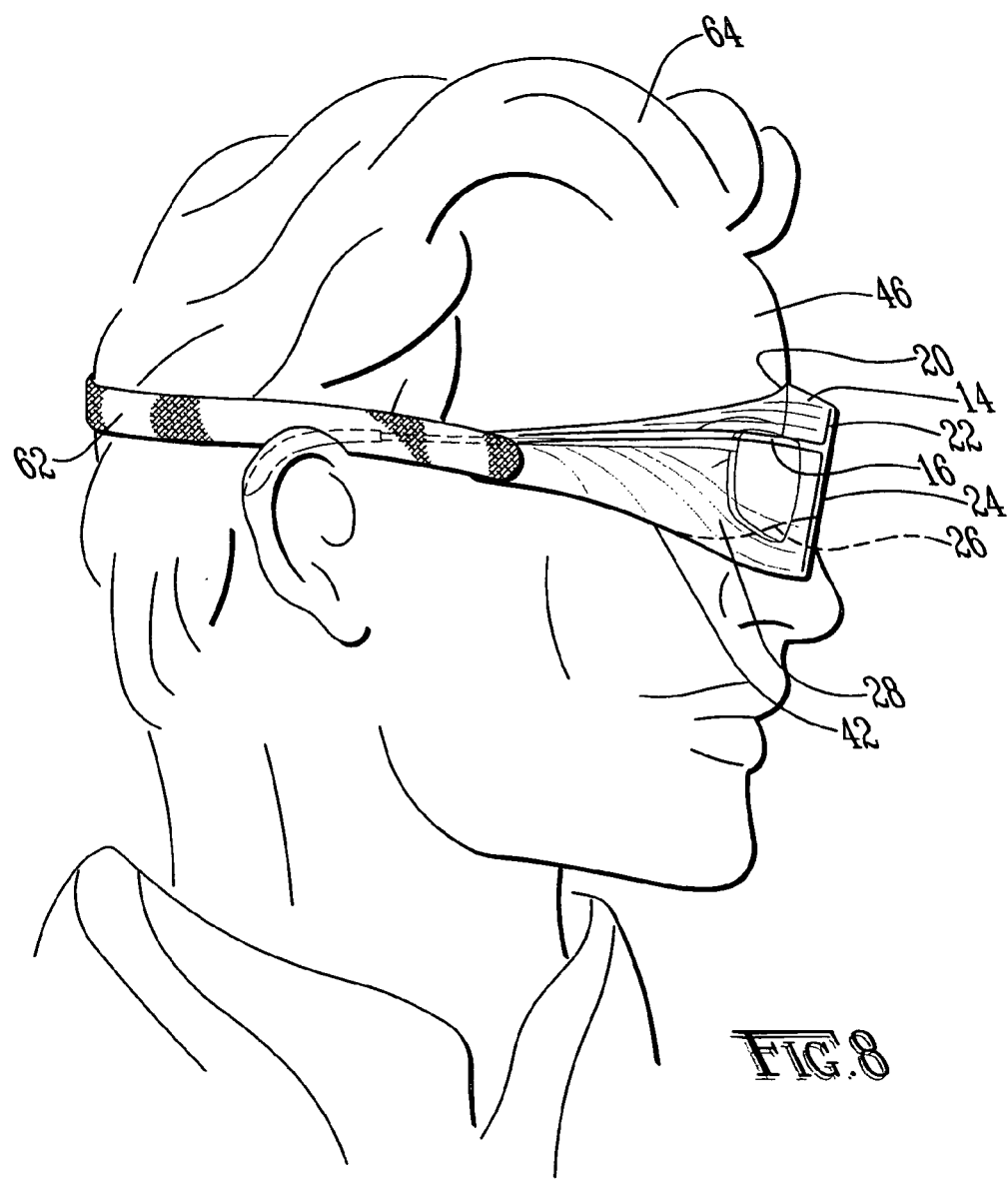
FIG. 8 is an side elevation view of a multi-purpose goggle of the present invention positioned on the face of a wearer.

As shown in FIG. 8, the preferred embodiment of the goggle 10 is sufficiently offset from the face 46 of the wearer to accommodate a wide range of eye glasses 60. As shown in FIG. 7, a preferred embodiment of the goggle 10 is sufficiently spacious to accommodate a pair of glasses 60 without interference between the lenses 70 and frame 72 with the interior 74 of the goggle.

The goggle 10 upper surface 14 and lower panels 28, 30 are preferably formed of a shatter resistant material 1–5 mm in thickness; however, other dimensions may be employed based upon the need of the individual wearer. Examples of the shatter resistant materials include, but are not limited to polycarbonates. In the preferred embodiment of the invention, the upper surface 14 and lower panels 28, 30 are preferably formed as a single unified component and can be produced using standard injection molding techniques. Additionally, in a preferred translucent embodiment, the joining of the first and second ends 16, 18 of the upper surface 14 to the first and second lower panels 28, 30 is performed in such a fashion to avoid the formation of a joint or seam that could detract from the ability of the wearer to see out through the ends 16, 18.

The multi-purpose goggles are manufactured in a fashion that produces a downwardly extending upper surface 14 with a first end 16 and a second end 18, a centrally disposed open frontal area 24, a centrally disposed nose bridge 26, a first and second lower panel 48, 50 disposed opposite the nose bridge, the first and second lower panels 48, 50 connecting with the upper surface first and second ends 16, 18. The multi-purpose goggle is further provided with a securing apparatus comprising support arms 52, 54 and a headband 62 for securing the goggle 10 onto the head of the wearer 64.

While this invention is susceptible of embodiments in many different forms, this specification and the accompanying drawings disclose only preferred embodiments of the invention. The invention is not intended to be limited to the embodiments so described, and the scope of the invention will be pointed out in the appended claims.

What is claimed is:

1. A multi-purpose goggle comprising:
    a downwardly extending upper surface with a first end and a second end;
    a centrally disposed viewing area;
    a centrally disposed nose bridge;
    a first and second upwardly extending lower panel disposed opposite the nose bridge, an upper edge of the first and second lower panel connecting with the upper surface first and second ends;
    a posterior edge of the upper surface and a posterior edge of the first and second lower panels contoured to conform to the topography of the wearer's face; and
    a securing apparatus for securing the goggle to the head of the wearer, the securing apparatus comprising a rearward extension of the upper surface and lower first and second panels.

2. The goggle according to claim 1, wherein vents are disposed adjacent the nose bridge to facilitate air flow into and out of the housing.

3. The goggle according to claim 1, wherein the upper surface and the first and second lower panels are comprised of a transparent material.

4. The goggle according to claim 1, wherein the upper surface and the first and second lower panels are comprised of an opaque material.

5. The goggle according to claim 1, wherein the securing apparatus is operatively coupled to a head encompassing device.

6. The goggle according to claim 1, wherein the centrally disposed viewing area is operatively configured for receiving an insert.

7. The goggle according to claim 6, wherein the insert is translucent.

8. The goggle according to claim 6, wherein the insert is opaque.

9. The goggle according to claim 6, wherein the insert occupies the entire centrally disposed viewing area of the goggle.

10. The goggle according to claim 6, wherein the insert occupies only a portion of the centrally disposed viewing area of the goggle.

11. The goggle according to claim 1, wherein the upper surface extends sufficiently outward from the face of the wearer to accommodate a wide range of eyeglass frame sizes on the head of the wearer.

12. The goggle according to claim 1, wherein the centrally disposed viewing area is operatively configured for receiving a virtual reality display device.

13. The goggle according to claim 1, wherein as measured from a center point of the upper surface, the upper surface extends downwardly from the horizontal at an angle ranging between 10 and 40 degrees.

14. The goggle according to claim 13, wherein as measured from a center point of the upper surface, the upper surface extends downwardly from the horizontal at an angle preferably ranging between 20 and 30 degrees.

15. A method for making a multi-purpose goggle, the method comprising the steps of:
    producing a goggle with a downwardly extending upper surface with a first end and a second end, a centrally disposed viewing area, a centrally disposed nose bridge, a first and second lower panel upwardly extending toward the upper surface disposed opposite the nose bridge from one another wherein an upper edge of the first and second lowers panel join with the upper surface first and second end;
    providing a posterior edge of the upper surface and first and second lower panels contoured to conform to the topography of the wearer's face; and
    providing a securing apparatus for securing the goggle onto the head of the wearer, the securing apparatus comprising a rearward extension of the upper surface and first and second lower panels.

16. The method according to claim 15, wherein vents for exhausting moisture are disposed adjacent the nose bridge.

17. The method according to claim 15, wherein the upper surface and first and second lower panels are comprised of an opaque material.

18. The method according to claim 15, wherein the upper surface and first and second lower panels are comprised of a translucent material.

19. The method according to claim 15, wherein the securing apparatus is operatively coupled to a head encompassing device.

20. The method according to claim 15, wherein the centrally disposed viewing area is operatively configured for receiving an insert.

21. The method according to claim 20, wherein the insert is opaque.

22. The method according to claim 20, wherein the insert is translucent.

23. The method according to claim 20, wherein the insert occupies the entire centrally disposed viewing area.

24. The method according to claim 20, wherein the insert occupies only a portion of the centrally disposed viewing area.

25. The method according to claim 15, wherein the viewing area is disposed sufficiently outward from the face of the wearer to accommodate the glasses of a wearer.

26. The method according to claim 15, wherein a posterior edge of the upper and lower panels are padded to increase wearer comfort.

27. A goggle comprising:
    an upper surface joined to a first and second lower panel, the upper surface extending downwardly from a first posterior edge adjacent to and conforming to the forehead of the wearer and traversing from one side of the wearer's face to the other, the first and second lower panels extending upwardly from a second posterior edge adjacent to and conforming to the face of the wearer;
    a centrally disposed viewing area;

a centrally disposed nose bridge; and a securing apparatus for securing the goggle to the head of the wearer, the securing apparatus comprising a rearward extension of the upper surface and first and second lower panels.

28. The goggle according to claim 27, wherein vents are disposed adjacent the nose bridge to facilitate air flow into and out of the housing.

29. The goggle according to claim 27, wherein the upper surface and the first and second lower panels are comprised of a transparent material.

30. The goggle according to claim 27, wherein the upper surface and the first and second lower panels are comprised of an opaque material.

31. The goggle according to claim 27, wherein the securing apparatus is operatively coupled to a head encompassing device.

32. The goggle according to claim 27, wherein the centrally disposed viewing area is operatively configured for receiving an insert.

33. The goggle according to claim 32, wherein the insert is translucent.

34. The goggle according to claim 32, wherein the insert is opaque.

35. The goggle according to claim 32, wherein the insert occupies the entire centrally disposed viewing area.

36. The goggle according to claim 32, wherein the insert occupies only a portion of the centrally disposed viewing area.

37. The goggle according to claim 27, wherein the housing extends sufficiently outward from the face of the wearer to accommodate a wide range of eyeglass frame sizes on the head of the wearer.

38. The goggle according to claim 27, wherein a posterior edge of the upper surface and lower panels are padded to increase wearer comfort.

39. The goggle according to claim 27, wherein the centrally disposed viewing area is permanently enclosed.

40. A goggle comprising:

an upper surface joined to a first and second lower panel, the upper surface extending downwardly from a first posterior edge adjacent to and conforming to the forehead of the wearer and traversing from one side of the wearer's face to the other, the first and second lower panels extending upwardly to join with the upper surface from a second posterior edge adjacent to and conforming to the face of the wearer;

at least one viewing area;

a centrally disposed nose bridge; and a securing apparatus for securing the goggle to the head of the wearer, the securing apparatus comprising a rearward extension of the upper surface and first and second lower panels.

41. A goggle for maximizing the field of vision of the wearer, the goggle comprising:

a translucent upper surface joined to a translucent first and second lower panel, the translucent upper surface extending downwardly from a first posterior edge adjacent to and conforming to the forehead of the wearer and traversing from one side of the wearer's face to the other, the first and second lower translucent panels extending upwardly to join with the upper surface from a second posterior edge adjacent to and conforming to the face of the wearer;

at least one viewing area;

a centrally disposed nose bridge; and a securing apparatus for securing the goggle to the head of the wearer, the securing apparatus comprising a rearward extension of the translucent upper surface and translucent first and second lower panels.

* * * * *